US009138403B2

(12) United States Patent
Del Rio et al.

(10) Patent No.: US 9,138,403 B2
(45) Date of Patent: Sep. 22, 2015

(54) PEG-INTERFERON-BETA FORMULATIONS (75) Inventors: Alessandra Del Rio, Rome (IT); Joel Richard, Montfort L'Amaury (DE)

(73) Assignee: MERCK SERONO SA, Coinsins, Vaud (CH)

( * ) Notice: Subject to any disclaimer, the term of this patent is extended or adjusted under 35 U.S.C. 154(b) by 907 days.

(21) Appl. No.: 12/738,375

(22) PCT Filed: Dec. 18, 2008

(86) PCT No.: PCT/EP2008/067876
§ 371 (c)(1),
(2), (4) Date: Apr. 16, 2010

(87) PCT Pub. No.: WO2009/080699
PCT Pub. Date: Jul. 2, 2009

(65) Prior Publication Data
US 2010/0239529 A1  Sep. 23, 2010

Related U.S. Application Data (60) Provisional application No. 61/010,258, filed on Jan. 7, 2008.

(30) Foreign Application Priority Data

Dec. 20, 2007  (EP) ..................................... 07150258

(51) Int. Cl.
A61K 38/21 (2006.01)
A61K 47/26 (2006.01)
A61K 47/34 (2006.01)
A61K 38/00 (2006.01)
C07K 14/565 (2006.01)
A61K 9/00 (2006.01)
C07K 14/555 (2006.01)
A61K 47/48 (2006.01)

(52) U.S. Cl.
CPC ............... *A61K 9/0019* (2013.01); *A61K 38/21* (2013.01); *A61K 38/215* (2013.01); *A61K 47/26* (2013.01); *A61K 47/34* (2013.01); *A61K 47/48215* (2013.01); *C07K 14/555* (2013.01); *C07K 14/565* (2013.01); *A61K 2300/00* (2013.01)

(58) Field of Classification Search
CPC ... A61K 38/21; A61K 38/215; A61K 9/0019; A61K 47/26; A61K 47/10; C07K 14/555
See application file for complete search history.

(56) References Cited

U.S. PATENT DOCUMENTS

| 4,432,895 A | 2/1984 | Tarnowski |
| 4,469,228 A | 9/1984 | Zupon et al. |
| 4,588,585 A | 5/1986 | Mark et al. |
| 4,695,623 A | 9/1987 | Stabinsky |
| 4,737,462 A | 4/1988 | Mark et al. |
| 4,879,111 A | 11/1989 | Chong |
| 4,897,471 A | 1/1990 | Stabinsky |
| 4,904,584 A | 2/1990 | Shaw |
| 4,959,314 A | 9/1990 | Mark et al. |
| 4,965,195 A | 10/1990 | Namen et al. |
| 5,017,691 A | 5/1991 | Lee et al. |
| 5,116,943 A | 5/1992 | Koths et al. |
| 5,346,696 A | 9/1994 | Kim et al. |
| 5,541,293 A | 7/1996 | Stabinsky |
| 5,762,923 A | 6/1998 | Gross et al. |
| 5,814,485 A | 9/1998 | Dorin et al. |
| 5,858,001 A | 1/1999 | Tsals et al. |
| 5,917,021 A | 6/1999 | Lee |
| 5,997,856 A | 12/1999 | Hora et al. |
| 6,013,253 A | 1/2000 | Martin et al. |
| 6,130,200 A | 10/2000 | Brodbeck et al. |
| 6,531,122 B1 | 3/2003 | Pedersen et al. |
| 6,569,420 B2 | 5/2003 | Chen et al. |
| 6,582,728 B1 | 6/2003 | Platz et al. |
| 6,852,314 B1 | 2/2005 | Samaritani et al. |
| 6,923,956 B1 | 8/2005 | Tschope et al. |
| 2002/0172661 A1 | 11/2002 | Shirley et al. |
| 2003/0138491 A1 | 7/2003 | Tracy et al. |
| 2005/0186177 A1 | 8/2005 | Michael et al. |
| 2006/0014666 A1 | 1/2006 | Ji et al. |
| 2006/0051320 A1 | 3/2006 | Shameem et al. |
| 2007/0032408 A1* | 2/2007 | Holmes et al. ..................... 514/9 |
| 2007/0059285 A1 | 3/2007 | Samaritani et al. |
| 2007/0092487 A1 | 4/2007 | Samaritani et al. |

(Continued)

FOREIGN PATENT DOCUMENTS

| EP | 0098110 B1 | 1/1984 |
| EP | 0177153 B1 | 4/1986 |

(Continued)

OTHER PUBLICATIONS

Arduini, R.M. et al. "Expression, purification, and characterization of rat interferon-β, and preparation of an N-terminally PEGylated form with improved pharmacokinetic parameters" *Protein Expression and Purification*, 2004, pp. 229-242, vol. 34.
Baker, D.P. et al. N-terminally PEGylated Human Interferon- β-1a with Improved Pharmacokinetic Properties and in Vivo Efficacy in a Melanoma Angiogenesis Model *Bioconjugate Chem.*, 2006, pp. 179-188, vol. 17, XP-002497163.
Derynck, R. et al. "Isolation and structure of a human fibroblast interferon gene" *Nature*, Jun. 19, 1980, pp. 542-547, vol. 285.
Familletti, P.C. et al. "A Convenient and Rapid Cytopathic Effect Inhibition Assay for Interferon" *Methods in Enzymology*, 1981, pp. 387-394, vol. 78.
Mager, D.E. et al. "Pharmacokinetics and Pharmacodynamics of PEGylated IFN- β 1a Following Subcutaneous Administration in Monkeys" *Pharmaceutical Research*, Jan. 2005, pp. 58-61, vol. 22, No. 1.
Mark, D.E. et al. "Site-specific mutagenesis of the human fibroblast interferon gene" *Proc. Natl. Acad. Sci. USA*, Sep. 1984, pp. 5662-5666, vol. 81.

(Continued)

*Primary Examiner* — Robert Landsman
*Assistant Examiner* — Bruce D Hissong
(74) *Attorney, Agent, or Firm* — Saliwanchik, Lloyd & Eisenschenk (57) ABSTRACT

The invention relates to a liquid pharmaceutical composition comprising a pegylated IFN-β (PEG-IFN-β), an excipient, a surfactant and a buffer wherein said excipient is a polyol, wherein said surfactant is a non-ionic surfactant and wherein said buffer is a sodium acetate buffer.

29 Claims, 3 Drawing Sheets

(56) References Cited

U.S. PATENT DOCUMENTS

| | | |
|---|---|---|
| 2007/0104682 A1 | 5/2007 | Del Curto |
| 2007/0244299 A1 | 10/2007 | Jaber |
| 2007/0248674 A1 | 10/2007 | Del Curto et al. |
| 2007/0292391 A1 | 12/2007 | Samaritani et al. |

FOREIGN PATENT DOCUMENTS

| | | |
|---|---|---|
| EP | 0509968 B1 | 10/1992 |
| EP | 736303 | 10/1996 |
| EP | 1224940 | 9/1998 |
| EP | 1250932 | 10/2002 |
| EP | 1666496 | 12/2002 |
| WO | WO 90/03784 A1 | 4/1990 |
| WO | WO 95/31213 | 11/1995 |
| WO | WO 98/28007 | 7/1998 |
| WO | WO 99/48535 | 9/1999 |
| WO | WO 99/55377 A3 | 11/1999 |
| WO | WO 00/23114 | 4/2000 |
| WO | WO 00/24374 A1 | 5/2000 |
| WO | WO 01/03737 A1 | 1/2001 |
| WO | WO 01/58474 A2 | 8/2001 |
| WO | WO 02/03472 A2 | 1/2002 |
| WO | WO 02/09766 A1 | 2/2002 |
| WO | WO 02/051386 A2 | 7/2002 |
| WO | WO 03/002152 | 1/2003 |
| WO | WO 03/066585 A2 | 8/2003 |
| WO | WO 2004/002404 A2 | 1/2004 |
| WO | WO 2004/050101 | 6/2004 |
| WO | WO 2004/060299 | 7/2004 |
| WO | WO 2004/096263 | 11/2004 |
| WO | WO 2005/084303 | 9/2005 |
| WO | WO 2005/110466 | 11/2005 |
| WO | WO 2005/117949 A1 | 12/2005 |

OTHER PUBLICATIONS

Pepinsky, R.B. et al. "Improved Pharmacokinetic Properties of a Polyethylene Glycol-Modified Form of Interferon- β-1a with Preserved in Vitro Bioactivity" *Journal of Pharmacology and Experimental Therapeutics*, 2001, pp. 1059-1066, vol. 297, No. 3, XP-002982987.
Pestka, S. "Interferon Standards and General Abbreviations" *Methods in Enzymology*, 1986, pp. 14-23, vol. 119.
Rubinstein, S. et al. "Convenient Assay for Interferons" *Journal of Virology*, Feb. 1981, pp. 755-758, vol. 37, No. 2.
Shepard, H.M. et al. "A single amino acid change in IFN- $β_1$ abolishes its antiviral activity" *Nature*, Dec. 10, 1981, pp. 563-565, vol. 294.
Woghiren, C. et al. "Protected Thiol-Polyethylene Glycol: A New Activated Polymer for Reversible Protein Modification" *Bioconjugate Chem.*, 1993, pp. 314-318, vol. 4.
Zhao, H. et al. "Linear and Branched Bicin Linkers for Releasable PEGylation of Macromolecules: Controlled Release in Vivo and in Vitro from Mono- and Multi-PEGylated Proteins" *Bioconjugate Chem.*, 2006, pp. 341-351, vol. 17, XP-002497164.
Written Opinion in International Application No. PCT/EP2008/067876, Oct. 5, 2009, pp. 1-9.
Hultgren, C. et al. "The Antiviral Compound Ribavirin Modulates the T Helper (Th) 1/Th2 Subset Balance in Hepatitis B and C Virus-Specific Immune Responses", *Journal of General Virology*, 1998, pp. 2381-2391, vol. 79.
Brewster, M. E. et al. "Use of 2-Hydroxypropyl-β-cyclodextrin as a Solubilizing and Stabilizing Excipient for Protein Drugs", *Pharmaceutical Research*, 1991, pp. 792-795, vol. 8, No. 6.
Arakawa, T. et al. "Factors affecting short-term and long-term stabilities of proteins" *Advanced Drug Delivery Reviews*, 2001, pp. 307-326, vol. 46, Nos. 1-3.
Irie, T. et al. "Cyclodextrins in peptide and protein delivery" *Advanced Drug Delivery Reviews*, 1999, pp. 101-123, vol. 36.
Bromberg, L. E. et al. "Temperature-responsive Gels and Thermogelling Polymer Matrices for Protein and Peptide Delivery", *Advanced Drug Delivery Reviews*, 1998, pp. 197-221, vol. 31.
Chen-Chow, P.-C. et al. "In Vitro Release of Lidocaine from Pluronic F-127 Gels", *International Journal of Pharmaceutics*, 1981, pp. 89-99, vol. 8.
Gander, B. et al. "Crosslinked Poloxamers as a Versatile Monolithic Drug Delivery System", *Drug Devel. and Indust. Pharmacy*, 1986, pp. 1613-1623, vol. 12, Nos. 11-13.
Guzmán, M. et al. "Polyoxyethylene-polyoxypropylene Block Copolymer Gels as Sustained Release Vehicles for Subcutaneous Drug Administration", *International Journal of Pharmaceutics*, 1992, pp. 119-127, vol. 80.
Johnston, T. P. et al. "Sustained Delivery of Interleukin-2 from a Poloxamer 407 Gel Matrix Following Intraperitoneal Injection in Mice", *Pharmaceutical Research*, 1992, pp. 425-434, vol. 9, No. 3.
Katakam, M. et al. "Controlled Release of Human Growth Hormone in Rats Following Parenteral Administration of Poloxamer Gels", *Journal of Controlled Release*, 1997, pp. 21-26, vol. 49.
Miyazaki, S. et al. "Pluronic F-127 Gels as a Novel Vehicle for Rectal Administration of Indomethacin", *Chem. Pharm. Bull.*, 1986, pp. 1801-1808, vol. 34, No. 4.
Schmolka, I. R. "A Review of Block Polymer Surfactants", *Journal of the American Oil Chemists' Society*, Mar. 1977, pp. 110-116, vol. 54.
Stewart, W. E. et al. "Interferon Nomenclature", *J. Interferon Res.*, 1980, pp. vi-vii, vol. 1.
Stratton, L. P. et al. "Drug Delivery Matrix Containing Native Protein Precipitates Suspended in a Poloxamer Gel", *Journal of Pharmaceutical Sciences*, Sep. 1997, pp. 1006-1010, vol. 86, No. 9.
Database WPI, Section Ch, Week 200406, Derwent Publicatons, Ltd., AN 2004-056676, XP-002301962 "Formulation for Injection of Interferon, Contains Interferon-alpha and Polyoxyethylene Polyoxypropylene Glycol", Dec. 3, 2003, 1 page.
Polman, C. H. et al. "Drug Treatment of multiple sclerosis" *BMJ*, Aug. 2000, pp. 490-494, vol. 321.
Prisms Study Group "Randomised double-blind placebo-controlled study of interferon β-1a in relapsing/remitting multiple sclerosis" *The Lancet*, Nov. 7, 1998, pp. 1498-1504, vol. 352.
Clegg, A. et al. "Immunomodulatory drugs for multiple sclerosis: a systematic review of clinical and cost effectiveness" *Exp. Opin. Pharmacother.*, 2001, pp. 623-639, vol. 2, No. 4.
McCormick, J. B. et al. "Lassa Fever effective therapy with ribavirin" *The New England Journal of Medicine*, Jan. 2, 1986, pp. 20-26, vol. 314, No. 1.
Cook, S. D. "Advancing Treatment with Interferon beta-1b (Betaferon®/Betaseron®) in the Next Decade", *J. Neurol.*, 2003, pp. IV/15-IV/20, vol. 25, Suppl. 4.
Lam, X. M. et al. "The Effect of Benzyl Alcohol on Recombinant Human Interferon-γ", *Pharmaceutical Research*, 1997, pp. 725-729, vol. 14, No. 6.
Schuck, P. "Size-Distribution Analysis of Macromolecules by Sedimentation Velocity Ultracentrifugation and Lamm Equation Modeling", *Biophysical Journal*, Mar. 2000, pp. 1606-1619, vol. 78.
Wang, Y.-C. J. et al. "Parenteral Formulations of Proteins and Peptides: Stability and Stabilizers", *Journal of Parenteral Science & Technology*, 1988, pp. S4-S26, vol. 42.
Wang, W. "Instability, Stabilization, and Formulation of Liquid Protein Pharmaceuticals", *International Journal of Pharmaceutics*, 1999, pp. 129-188, vol. 185.
Office Action dated Mar. 23, 2009 in U.S. Appl. No. 11/596,599, filed Nov. 15, 2006.
Office Action dated Nov. 6, 2009 in U.S. Appl. No. 11/596,599, filed Nov. 15, 2006.
Office Action dated Mar. 27, 2009 in U.S. Appl. No. 11/597,987, filed Nov. 30, 2006.
Office Action dated Sep. 17, 2009 in U.S. Appl. No. 11/597,987, filed Nov. 30, 2006.
Office Action dated Jun. 23, 2009 in U.S. Appl. No. 11/597,982, filed Nov. 30, 2006.
Office Action dated Mar. 19, 2010 in U.S. Appl. No. 11/597,982, filed Nov. 30, 2006.
Office Action dated Apr. 2, 2009 in U.S. Appl. No. 10/554,602, filed Oct. 16, 2006.
Office Action dated Jun. 23, 2009 in U.S. Appl. No. 10/582,027, filed Jun. 8, 2006.
Office Action dated Jan. 25, 2010 in U.S. Appl. No. 10/582,027, filed Jun. 8, 2006.

* cited by examiner

PEG-INTERFERON-BETA FORMULATIONS

CROSS-REFERENCE TO RELATED APPLICATIONS

This application is the U.S. national stage application of International Patent Application No. PCT/EP2008/067876, filed Dec. 18, 2008, which claims the benefit of U.S. Provisional Patent Application No. 61/010,258, filed Jan. 7, 2008.

FIELD OF THE INVENTION

The present invention relates to formulations of pegylated Interferon-beta (PEG-IFN-β).

BACKGROUND OF THE INVENTION

Interferon-β is a protein and has been identified as useful medicament applied today e.g. for the treatment of Multiple Sclerosis (MS).

Proteins can be modified either in their sequence or by other modifications in order to alter or improve e.g. their activity or stability. One such modification is the introduction of a linkage to polymers like polyethylene glycol (PEG).

Interferon-β linked to polyethylene glycol (PEG-IFN-β) has been described e.g. in WO99/55377 and EP 0 593 868 A1.

In the medical field, various approaches have been taken to stabilize proteins by lyophilization or in the form of liquid pharmaceutical composition. Lyophylized materials have to be reconstituted in a solution prior to use. Easier and thus of particular interest are concentrated or ready-to-use liquid pharmaceutical composition that do not need any further preparation for their application to the patient.

Pharmaceutical liquid formulations of interferon-β are e.g. described in WO95/31213 and WO2004/096263.

WO2005/084303 describes interferon-beta 1b-polymer conjugate compositions.

U.S. Pat. No. 6,531,122 is concerned with pegylated interferon variants in a formulation with excipients, solubilizers and a buffer.

WO2004/060299 provides methods for the synthesis of polymer conjugates of cytokines including interferon-beta and receptor-binding antagonists thereof.

US20060051320 A1 relates to lyophilized formulations of pegylated interferon prepared using trehalose as cryoprotectant.

WO99/48535 provides formulations that prevent loss and damage of PEG-interferon alpha conjugates during and following lyophilization.

WO03002152 relates in particular to stabilized compositions comprising an interferon polypeptide and a sulfoalkyl ether cyclodextrin derivative.

None of the above references discloses or suggests the liquid formulations according to the invention.

SUMMARY OF THE INVENTION

According to one aspect of the invention, is provided a liquid pharmaceutical composition comprising a pegylated interferon-beta (PEG-IFN-β), an excipient, a surfactant and a buffer wherein said excipient is a polyol, wherein said surfactant is a non-ionic surfactant and wherein said buffer is a sodium acetate buffer.

According to another aspect of the invention, is provided a method for preparing a liquid pharmaceutical composition, wherein said method comprises adding a calculated amount of excipient and surfactant to the buffered solution and then adding the PEG-IFN-β.

According to another aspect of the invention, is provided a container hermetically sealed in conditions sterile and appropriate for storage prior to use, comprising the liquid pharmaceutical formulation according to the invention.

According to another aspect of the invention, is provided a kit of a pharmaceutical composition, wherein the kit comprises a container filled with a pharmaceutical composition according to the invention.

BRIEF DESCRIPTION OF THE TABLES AND FIGURES

I. Formulations According to the Invention containing 0.044 mg/ml PEG-IFN-beta.

Table 1 depicts various formulations according to the invention containing 0.044 mg/ml PEG-IFN-beta.

Table 2 describes a stability test (SE-HPLC) at 40° C., 25° C. and 2-8° C., respectively, of formulations according to the invention with a pH of 4.2 over time.

Table 3 describes a stability test (RP-HPLC) at 40° C., 25° C. and 2-8° C., respectively, of formulations according to the invention with a pH of 4.2 over time.

Table 4 depicts titres (mcg/mL) of formulations according to the invention by SE-HPLC.

Table 5 depicts titres (mcg/mL) of formulations according to the invention by SE-HPLC; before and after filtration with % recovery and a representation as a graph (FIG. 1: % recovery shown as AF and TO recovery in %).

Table 6 shows the pH values of formulations according to the invention over 4 to 26 weeks at 25° C. and 2-8° C., respectively.

Table 7 depicts bioassay results of formulations according to the invention over time.

II. Formulations According to the Invention Containing 0.055 and 0.110 mg/ml PEG-IFN-beta, Respectively.

These formulations the PEG-IFN-beta amount has been increased to 0.055 and 0.110 mg/ml PEG-IFN-beta 1a, respectively.

Table 8 depicts a SE-HPLC test measuring purity at 40° C., 25° C. and 2-8° C., respectively, of formulations according to the invention with a pH of 4.2 over time.

Table 9 depicts a SE-HPLC test measuring protein content at 40° C., 25° C. and 2-8° C., respectively, of formulations according to the invention with a pH of 4.2 over time.

Table 10 depicts RP-HPLC test measuring purity 40° C., 25° C. and 2-8° C., respectively, of formulations according to the invention with a pH of 4.2 over time.

Table 11 shows the pH values of formulations according to the invention over 4 to 13 weeks at 25° C. and 2-8° C., respectively, over time.

Table 12 shows bioassay data of formulations according to the invention at 25° C. and 2-8° C., respectively, over time.

Table 13 depicts data regarding oxidized forms by peptide mapping of PEG-IFN-beta of formulations according to the invention.

DETAILED DESCRIPTION OF THE INVENTION

The invention relates to a liquid pharmaceutical composition comprising a pegylated interferon-beta (PEG-IFN-β, PEG-IFN-beta), an excipient, a surfactant and a buffer wherein said excipient is a polyol, wherein said surfactant is a non-ionic surfactant and wherein said buffer is a sodium acetate buffer.

In one aspect the invention relates to a liquid pharmaceutical composition comprising a PEG-IFN-β or muteins thereof or active fragments thereof, an excipient, a surfactant and a buffer wherein said excipient is a polyol, wherein said surfactant is a non-ionic surfactant and wherein said buffer is a sodium acetate buffer.

The following paragraphs provide definitions of the various compounds that make up the formulation according to the invention and are intended to apply uniformly through-out the specification and claims unless an otherwise expressly set out definition provides a broader definition.

Pegylated interferon-beta of the formulation may be any interferon-beta that bears as covalent modification a polyethylene glycol or a comparable modification. One example of a PEG-interferon-beta is a PEG-interferon-beta wherein PEGylation may be carried out by known methods, such as the ones described in WO99/55377.

In particular, according to the invention IFN-beta has covalently attached the hydrophilic polymer polyethylene glycol (PEG), also known as polyethylene oxide (PEO). The PEG may be a linear polymer having hydroxyl groups at each terminus:

$HOCH_2CH_2-O-(CH_2CH_2O)nCH_2CH_2OH$

It may be also used as methoxy-PEG-OH (m-PEG), in which one terminus is the relatively inert methoxy group, while the other terminus is a hydroxyl group that is subject to the chemical modification:

$CH_3O(CH_2CH_2O)nCH_2CH_2OH$

In the above n may be 1 to several hundred.

In another preferred embodiment the PEG may also be a branched PEG represented by R(PEG-OH)m wherein R represents a central coremoiety such as pentaerythriol or glycerol, and m represents the number of branching arms. The branching arms (m) can range from three to hundred or several hundred. The hydroxyl groups are subject to chemical modifications.

Another form of branching according to the invention is described e.g. in WO96/21469 wherein the PEG has a single terminus that is subject to chemical modification. This PEG type can be represented as $(CH_3OPEG)pRX$ wherein p equals 2 or 3, R represents a central core such as lysine or glycerol, and X represents a functional group such as carboxyl that is subject to chemical activation.

Another form of branching according to the invention is denoted "pendant PEG" and has reactive groups, such as carboxyl, along the PEG backbone rather than at the end of the PEG chains.

It is in addition possible to prepare the PEG-IFN-beta according to the invention with weak or degradable linkages in the backbone as e.g. described in U.S. patent application 06/026,716. Accordingly, PEG can be prepared with ester linkages in the polymer backbone that are subject to hydrolysis. The hydrolysis results in cleavage of the polymer into fragments of lower molecular weight, according to the reaction scheme:

$PEG-CO_2-PEG+H_2O \rightarrow -PEG-CO_2H+HO-PEG-$

Copolymers of ethylene oxide and propylene oxide are closely related to PEG in their chemistry and according to the invention they can be used instead of PEG.

A variety of methods have been developed to PEGylate proteins. PEG can be attached to reactive groups found in the protein utilizing usually electrophilically activated PEG derivatives. One may use the α- or ε-amino groups found in lysine residues and the N-terminus resulting in a conjugate consisting of a mixture of products.

The conjugates consist preferably of a population of one to several PEG molecules attached per protein molecule ranging from one to the number of amino acids in the protein.

It is preferred to introduce site directed PEGylation in the IFN-beta as e.g. described in Woghiren et al. in Bioconjugate Chem., 4(5): 314-318, 1993, synthesizing a thiol-selective PEG derivative.

The IFN in one embodiment is specifically PEGylated. A specific PEGylation may be performed according to EP 675 201 at the N-terminal residue with e.g. mPEG-proprionaldehyde. Particularly preferred is a site-specific mono-PEGylation as described by Woghiren et al., Bioconjugate Chem., 4(5): 314-318, 1993.

An embodiment according to the invention is an IFN-beta bearing a mono-PEGylation covalently bound to Cys[17] as described in WO99/55377. The PEG moiety may be linear or branched, methoxy PEG, hydrolytically or enzymatically degradable PEG and one or more polyols and copolymers of PEG and PLGA (poly(lactic/glycolic acid)).

The cystein thiol group according to an embodiment of the invention may be reacted with a thiol-reacting PEGylating agent. It may be a PEG containing a functional group such as orthopyridyl disulfide, vinylsulfone, maleimide, iodoacetimide. Preferably the thiol-reactive PEGylating agent, is the orthopyridyl disulfide (OPSS) derivative of PEG. The PEGylating agent is used in its mono-methylated form where only one terminus is available for conjugation, or in bifunctional form where both termini are available for conjugation.

In a preferred embodiment reaction a IFN-β-Cys[17] is used and reacts according to the reaction scheme as described in this application. This reaction is site-specific to Cys[17] because the other two cystein residues in IFN-β (positions 31 and 141) form a disulfide bridge and are thus not accessible to the PEGylation. The PEG-IFN-β has an effective size equivalent to that of a protein with a molecular weight of 50 to 110 kDa, preferably about 70 kDa. In the site-specific IFN-β modification the PEG molecule attached has preferably a molecular weight greater than 20 kDa. In one embodiment the PEG molecule attached at the Cys[17] has 2×20 kDa attached via a spacer.

The spacer and the IFN form a IFN-PEG 2 kDa—OPSS according to the below scheme of synthesis.

Following PEGylation the solution is purified in order to separate the PEG-IFN-β from free spacer and/or PEG. Preferably this purification step is performed by ultrafiltration. The ultrafiltration is performed at a temperature of less than 10° C., preferably at 5+/−3° C., more preferably at 4° C. at basic conditions. In the purification step preferably NaOH 0.1 M is used. The resulting PEG-IFN-β solution contains less than 0.5 EU/ml endotoxins, preferably less than 0.25 EU/ml endotoxins.

In one embodiment the PEGylation is introduced into the IFN-β according to the following scheme:

In one embodiment a low molecular weight PEG moiety may be linked to the IFN-ft

A low molecular weight PEG moiety has the formula:

$$W-CH_2CH_2O(CH_2CH_2O)_nCH_2CH_2-X$$

wherein W and X are groups that independently react with an amine, sulfhydryl, carboxyl or hydroxyl functional group to attach the low molecular PEG moiety to IFN-β. W and X are preferably independently selected from orthopyridyl disulfide, maleimides, vinyl sulfones, iodoacetamides, amines, thiols, carboxyls, active esters, benzotriazole carbonates, p-nitrophenol carbonates, isocyanates, and biotin.

The low molecular weight PEG moiety preferably has a molecular weight of 100 to 5000 daltons. In a preferred embodiment it has 1000 to 3000 daltons, preferably 1500 to 2000 daltons and more preferably 2000 daltons.

The monofunctional or bifunctional PEG moiety for the attachment to the free terminus of a low molecular weight PEG that is attached to the IFN-β has preferably a molecular weight in the range of about 100 to 200 daltons. It is preferably a methoxy PEG, branched PEG, hydrolytically or enzymatically degradable PEG, pendant PEG or dendrimer PEG.

The monofunctional and bifunctional PEG furthermore has the formula:

$$Y-CH_2CH_2-O-(CH_2CH_2O)mCH_2CH_2-Z$$

where Y is reactive to a terminal group on the free terminus of the low molecular weight PEG moiety that is attached to IFN-β abd Z is —OCH$_3$ or a group reactive to form a bifunctional conjugate.

Thus, in a stepwise manner two or more PEG moieties can be used to produce PEG-IFN-β useful in the composition of the invention and for use as a medicament.

Advantageously, the disulfide bond between PEG and IFN-β is stable in the circulation and may be cleaved upon entry in the cell.

The PEG-IFN-β used in the formulation according to the invention has about the same or a higher interferon-β activity as compared to native interferon-β.

The excipient may be any polyol that together with the other components of the formulation results in a stable PEG-interferon-beta formulation. Examples of polyols are mannitol (PEARLITOL®), sorbitol (NEOSORB®), maltitol (MALTISORB), xylitol (XYLISORB) and maltitol (LYCASIN). A preferred polyol excipient is mannitol.

According to the invention a non-ionic surfactant is used. Non-ionic surfactants include polyol derivatives, polyoxyethylene esters and ethers, poloxamers, nonylphenyl ethers, polyvinyl alcohols, propylene glycol diacetate, alkanolamides. The non-ionic surfactant may be preferably a poloxamer. Poloxamer 188 is particularly preferred.

Any buffer may be used which is capable to maintain the pH at the chosen level. The buffer may be a sodium acetate buffer or PBS. Particularly preferred is a sodium acetate buffer.

In one embodiment the invention is a liquid pharmaceutical composition comprising a PEG-interferon-beta, an excipient, a surfactant and a buffer wherein said excipient is mannitol, wherein said surfactant is poloxamer 188 and wherein said buffer is sodium acetate buffer.

Interferon-beta may be naturally-occurring human interferon-beta or a recombinantly produced one bearing a pegylation according to the invention. Further, interferon-beta (IFN-β) according to the invention refers to glycoproteins produced by the body in response to a viral infection.

The interferon unit or International unit for interferon (U or IU, for international unit) has been reported as a measure of IFN activity defined as the amount necessary to protect 50% of the cells against viral damage. The assay that may be used to measure bioactivity is the cytopathic effect inhibition assay as described (Rubinstein, et al. 1981; Familletti, P. C., et al., 1981). In this antiviral assay for interferon about 1 unit/ml of interferon is the quantity necessary to produce a cytopathic effect of 50%. The units are determined with respect to the international reference standard for Hu-IFN-beta provided by the National Institutes of Health (Pestka, S. 1986).

Interferons are also called biologic response modifiers (BRMs), because they have an effect on the response of the organism to the tumor, affecting recognition via immunomodulation.

Human fibroblast interferon (IFN-β) has antiviral activity and can also stimulate natural killer cells against neoplastic cells. It is a polypeptide of about 20,000 Da induced by viruses and double-stranded RNAs. From the nucleotide sequence of the gene for fibroblast interferon, cloned by recombinant DNA technology, (Derynk et al. 1980) deduced the complete amino acid sequence of the protein. It is 166 amino acids long.

Rebif® (Merck Serono—recombinant human interferon-β, an interferon therapy for multiple sclerosis (MS), is interferon (IFN)-beta-1a, produced from mammalian cell lines. Its recommended International Non-proprietary Name (INN) is "Interferon beta-1a".

An "interferon beta" or "IFN-β", as used herein, is intended to include any molecule defined as such in the literature, comprising for example any types of IFN-βs mentioned in the above section. IFN-β suitable in accordance with the present invention is commercially available e.g. as Rebif® (Merck Serono), Avonex® (Biogen Idec) as long as it exhibits the linking sites for specific PEGylation. The use of interferon beta of human origin is also preferred in accordance with the present invention. The term interferon beta, as used herein, is intended to encompass salts, functional derivatives, variants, muteins, analogs and active fragments thereof.

The term "interferon-beta (IFN-β)", as used herein, is intended to include fibroblast interferon in particular of human origin, as obtained by isolation from biological fluids or as obtained by DNA recombinant techniques from eukaryotic host cells, as well as its salts, functional derivatives, variants, analogs and active fragments. Preferably IFN-beta is intended to mean Interferon beta-1a.

As used herein the term "muteins" refers to analogs of IFN-β and PEG-IFN-β in which one or more of the amino acid residues of a natural IFN-β are replaced by different amino acid residues, or are deleted, or one or more amino acid residues are added to the natural sequence of IFN-β, without changing considerably the activity of the resulting products as compared to the wild type IFN-β. These muteins are prepared by known synthesis and/or by site-directed mutagenesis techniques, or any other known technique suitable therefor. Preferred muteins include e.g. the ones described by Shepard et al. (1981) or Mark et al. (1984). In particular muteins according to the invention contain a Cys$^{17}$ while any of the above changes in the molecule may be present.

Any such mutein preferably has a sequence of amino acids sufficiently duplicative of that of IFN-β, such as to have substantially similar or even better activity to an IFN-β. The biological function of interferon is well known to the person skilled in the art, and biological standards are established and available e.g. from the National Institute for Biological Standards and Control (http://immunology.org/links/NIBSC).

Bioassays for the determination of IFN-β/PEG-IFN-β activity have been described. An IFN assay may for example be carried out as described by Rubinstein et al., 1981. Thus, it can be determined whether any given mutein has substantially a similar, or even a better, activity than IFN-β by means of routine experimentation.

Muteins of IFN-β and accordingly of PEG-IFN-β, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of polypeptides or proteins of the invention may include synonymous amino acids within a group, which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Examples of production of amino acid substitutions in proteins which can be used for obtaining muteins of PEG-IFN-β, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al). Specific muteins of IFN-beta have been described, for example by Mark et al., 1984.

"Functional derivatives" as used herein cover derivatives of PEG-IFN-β, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IFN-β, and do not confer toxic properties on compositions containing it. These derivatives may, for example, include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of PEG-IFN-β, or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has no significantly reduced activity as compared to the corresponding IFN.

The term "salts" herein refers to both salts of carboxyl groups and to acid addition salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the proteins (IFN) relevant to the present invention, i.e., the ability to bind to the corresponding receptor and initiate receptor signaling.

In a further embodiment, the fused protein contained in the composition of the invention comprises an Ig fusion. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO: 1) introduced between the sequence of IFN and the immunoglobulin sequence. The resulting fusion protein may have improved properties, such as an extended residence time in body fluids (half-life), increased specific activity, increased expression level, or the purification of the fusion protein is facilitated.

Preferably the PEG-IFN-beta is present in the composition at a concentration of about 0.1 mg/ml to about 0.01 mg/ml, preferably about 0.06 mg/ml to about 0.03 mg/ml and even more preferably at a concentration of about 0.044 mg/ml.

In another embodiment the PEG-IFN-beta is present in the formulation according to the invention in a concentration of 0.05 to 0.150 mg/ml, preferably 0.055 or 0.110 mg/ml.

The dosage used in the composition and which may be applied to an individual will vary depending upon a variety of factors, including pharmacokinetic properties, the route of administration, patient conditions and characteristics (sex, age, body weight, health, size), extent of symptoms, concurrent treatments, frequency of treatment and the effect desired.

Standard dosages of human IFN-beta/PEG-IFN-beta range from 80 000 IU/kg to 200 000 IU/kg per day, or 6 MIU (million international units) to 12 MIU per person per day, or 22 to 44 μg (microgram) IFN-beta equivalent per person. In accordance with the present invention, PEG-IFN-β in the composition of the invention may preferably be used at a dosage of about 1 to 50 μg, more preferably of about 10 to 30 μg or about 10 to 20 μg per person per day equivalent to IFN-beta.

The administration of active ingredients in accordance with the present invention may be by intravenous, intramuscular or subcutaneous route. Preferred routes of administration for the composition of the invention are the subcutaneous and intramuscular route.

The PEG-IFN-β composition of the invention may also be administered daily or every other day, or less frequent. Preferably, the PEG-IFN-β composition is administered one, twice or three times per week. Preferably it is administered once any two weeks.

The preferred route of administration is subcutaneous administration, administered e.g. three times a week. A further preferred route of administration is the intramuscular administration, which may e.g. be applied once a week.

Preferably 22 to 44 μg or 6 MIU to 12 MIU equivalent to IFN-beta of PEG-IFN-beta in the composition of the invention is administered three times a week by subcutaneous injection.

The PEG-IFN-beta composition may be administered subcutaneously, at a dosage of 25 to 30 μg or 8 MIU to 9.6 MIU, every other day. 30 μg or 6 MIU equivalent to IFN-beta of PEG-IFN-beta may further be administered intramuscularly once a week.

The term "stability" refers to the physical, chemical, and conformational stability of formulations of interferon of the present invention (including maintenance of biological potency). Instability of a protein formulation may be caused by chemical degradation or aggregation of the protein molecules to form higher order polymers, deglycosylation, modification of glycosylation, oxidation or any other structural modification that reduces at least one biological activity of an interferon polypeptide included in the present invention.

A "stable" composition, solution or formulation, is one wherein the degree of degradation, modification, aggregation, loss of biological activity and the like, of proteins therein is acceptably controlled, and does not increase unacceptably with time. Preferably the formulation retains at least at or about 60%, more preferably at least at or about 70%, most preferably at least at or about 80% of the labelled interferon activity over a period of from 12 to 24 months. The preferred PEG-IFN-β compositions of the invention preferably have a shelf-life of at least about 6 months, 12 months, 18 months, more preferably at least 20 months, still more preferably at least about 22 months, most preferably at least about 24 months when stored at 2-8° C.

Methods for monitoring stability of the liquid PEG-IFN-β pharmaceutical compositions of the invention are available in the art, including those methods described herein. Thus, PEG-IFN-β aggregate formation during storage of a liquid pharmaceutical composition of the invention can be readily determined by measuring the change in soluble PEG-IFN-β in solution over time. The amount of soluble polypeptide in solution can be quantified by a number of analytical assays adapted to detection of the particular PEG-IFN-β. Such assays include, for example, reverse phase (RP)-HPLC and UV absorption spectroscopy, as described in the Examples below.

Determination of both soluble and insoluble aggregates during storage in liquid compositions can be achieved, for example, using analytical ultracentrifugation as noted in the Examples below to distinguish between that portion of the soluble polypeptide that is present as soluble aggregates and that portion that is present in the non-aggregated, biologically active molecular form.

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation. Acceptable buffers for controlling pH at a moderately acidic pH include, but are not limited to, such compounds as phosphate, acetate, citrate, arginine, TRIS, and histidine. "TRIS" refers to 2-amino-2-hydroxymethyl-1,3-propanediol, and to any pharmacologically acceptable salt thereof. Preferable buffers are acetate buffers with saline or an acceptable salt.

The excipient is preferably present at a concentration of about 30 mg/ml to about 50 mg/ml, more preferably in a concentration of about 40 mg/ml to about 50 mg/ml, even more preferably in a concentration of about 45 mg/ml.

The surfactant has preferably a concentration of about 0.1 mg/ml to about 1 mg/ml, preferably a concentration of about 0.4 mg/ml to about 0.7 mg/ml, even more preferably a concentration of about 0.5 mg/ml.

The term "surfactant" refers to a soluble compound that reduces the surface tension of liquids, or reduces interfacial tension between two liquids or a liquid and a solid, the surface tension being the force acting on the surface of a liquid, tending to minimize the area of the surface. Surfactants have sometimes been used in pharmaceutical formulations, including delivery of low molecular mass drugs and polypeptides, in order to modify the absorption of the drug or its delivery to the target tissues. Well known surfactants include polysorbates (polyoxyethylene derivatives of sorbitol fatty esters; Tween®), as well as Poloxamers such as Pluronic® or Lutrol® marketed by BASF, Germany.

According to a preferred embodiment of the invention, it has been found that by formulating a PEG-IFN-β with a surfactant selected from Pluronic® F77, Pluronic® F87, Pluronic® F88 and Pluronic® F68, particularly preferably Pluronic® F68 (BASF, Pluronic® F68 is also known as Poloxamer 188) they obtain stable formulations that minimise the loss of active principle caused by adsorption on the surfaces of the vial and/or delivery device (e.g. syringe, pump, catheter, etc.). It has also been found that by formulating a PEG-IFN-β, with a surfactant selected from Pluronic® F77, Pluronic® F87, Pluronic® F88 and Pluronic® F68, particularly preferably Pluronic® F68 (BASF, Pluronic® F68 is also known as Poloxamer 188) they obtain a stable composition, which is more resistant to oxidation and to formation of protein aggregates.

The Pluronic® surfactants are block copolymers of ethylene oxide (EO) and propylene oxide (PO). The propylene oxide block (PO) is sandwiched between two ethylene oxide (EO) blocks.

In Pluronic® F77, the percentage of polyoxyethylene (hydrophile) is 70%, and the molecular weight of the hydrophobe (polyoxypropylene) is approximately 2,306 Da.

In Pluronic® F87, the percentage of polyoxyethylene (hydrophile) is 70%, and the molecular weight of the hydrophobe (polyoxypropylene) is approximately 2,644 Da.

In Pluronic® F88, the percentage of polyoxyethylene (hydrophile) is 80%, and the molecular weight of the hydrophobe (polyoxypropylene) is approximately 2,644 Da.

In Pluronic® F68, the percentage of polyoxyethylene (hydrophile) is 80%, and the molecular weight of the hydrophobe (polyoxypropylene) is approximately 1,967 Da.

Other polymers having properties similar to those of the pluronic series may also be used in the compositions of the invention. The preferred surfactant is Pluronic® F68, and surfactants having similar properties.

Pluronic, particularly Pluronic® F68, is preferably present at a concentration that is sufficient to maintain the stability of the PEG-IFN-β, over the desired storage period (for example 12 to 24 months), and also at a concentration that is sufficient to prevent protein losses due to adsorption on surfaces, such as the vial, ampoule or cartridge or the syringe.

Preferably the concentration of Pluronic®, particularly Pluronic® F68, in liquid formulations is at or about 0.01 mg/ml to at or about 10 mg/ml, more preferably at or about 0.05 mg/ml to at or about 5 mg/ml, more particularly preferably at or about 0.1 mg/ml to at or about 2 mg/ml, most preferably at or about 1 mg/ml.

In another preferred embodiment methionine is used, in particular L-methionine. Particularly useful is a concentration of 0.1 mg/ml to 0.5 mg/ml, preferably a concentration of about 0.1 mg/ml to 0.3 mg/ml, more preferably about 0.25 mg/ml or about 0.12 mg/ml.

It was found that by addition of methionine advantageously the formulation was further stabilized and oxidation of the protein was reduced.

The various compounds contained or comprised in the formulation according to the invention could be varied as described above and the positive effect of methionine could be achieved. In one embodiment the formulation is comprising or containing 0.055 mg/ml PEG-IFN-beta, 10 mM sodium acetate buffer at about pH 3.5 to 4.5, preferably pH 4.2, 45 mg/ml mannitol and 0.5 mg/ml poloxamer 188, alternatively 0.110 mg/ml PEG-IFN-beta.

The composition of the invention contains a buffer in an amount sufficient to maintain the pH of said composition within plus or minus 0.5 units of a specified pH, where the specified pH is about 3.0 to about 5.0, preferably said pH is about 3.5 to 4.5, even more preferably said pH is about 4.2±0.2.

The buffer is present in the composition of the invention at a concentration of about 5 mM to 500 mM, preferably in a concentration of about 10 mM.

The composition is preferably an aqueous solution.

The invention includes liquid compositions. The preferred solvent is water for injection.

It could be shown that by adjusting the pH to about pH 3 to 5, preferably to 3.5 to 4.5 and more preferably to about 4.2+/−0.2 for PEG-IFN-β compositions, stable formulations could be provided.

The compositions according to the invention achieved to positively influence the degradation process of the PEG-IFN-β which degradation process may be negatively influenced in liquid compositions. This influence may be measured by SE-HPLC at e.g. 40° C. and 25° C., respectively. The composition of the invention achieved that no significant decrease of PEG-IFN-β content (SE-HPLC) was observed. In particular, no decrease in PEG-IFN-β content was detected up to 2 weeks at 40° C. and up to 6 weeks at 25° C. The compositions of the invention exhibit good stability characteristics and in particular a reduction in protein aggregation upon storage could be achieved.

The positive results could in particular be achieved for a composition containing 0.044 mg/ml PEG-IFN-β, 10 mM sodium acetate buffer of about pH 4.2, mannitol 45 mg/ml and 0.5 mg/ml Poloxamer 188 prepared in glass vials, preferably 3 ml, or glass syringes, preferably 1 ml.

The compositions of the invention show good stability as measured by purity by use of SE-HPLC, RP-HPLC, protein content as measured by SE-HPLC and biological activity.

In another aspect the invention relates to a method for preparing a liquid pharmaceutical composition as described above, wherein said method comprises adding a calculated amount of excipient and surfactant to the buffered solution and then adding the PEG-IFN-β.

In yet another aspect the invention relates to a container hermetically sealed in conditions sterile and appropriate for storage prior to use, comprising the liquid pharmaceutical formulation according to the invention.

Any container appropriate for medical applications may be used. The container is preferably a pre-filled syringe, a vial or a cartridge for an auto-injector.

The formulations of the invention can be administered using recognized devices. Examples comprising these single vial systems include auto-injector or pen-injector devices for delivery of a solution such as Rebiject®.

The products presently claimed include packaging material. The packaging material provides, in addition to the information required by the regulatory agencies, the conditions under which the product may be used. The packaging material of the present invention provides instructions to the patient, if needed, to prepare the final solution and to use such final solution over a period of twenty-four hours or greater for the two vial, wet/dry, product. For the single vial, solution product, the label indicates that such solution may be used over a period of twenty-four hours or greater. The presently claimed products are useful for human pharmaceutical product use. The compositions may be provided to patients as clear solutions.

The PEG-IFN-β, may be administered to a patient in accordance with the present invention via a variety of delivery methods including SC or IM injection; transdermal, pulmonary, transmucosal, implant, osmotic pump, cartridge, micro pump, oral, or other means appreciated by the skilled artisan, as well-known in the art.

In another aspect the invention relates to a kit of a pharmaceutical composition, wherein the kit comprises a container filled with a pharmaceutical composition of the invention.

The container is preferably a syringe for use in a delivery device.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

In the following the present invention shall be illustrated by means of the examples, which are not construed to be limiting the scope of the invention.

EXAMPLES

Figure 1:
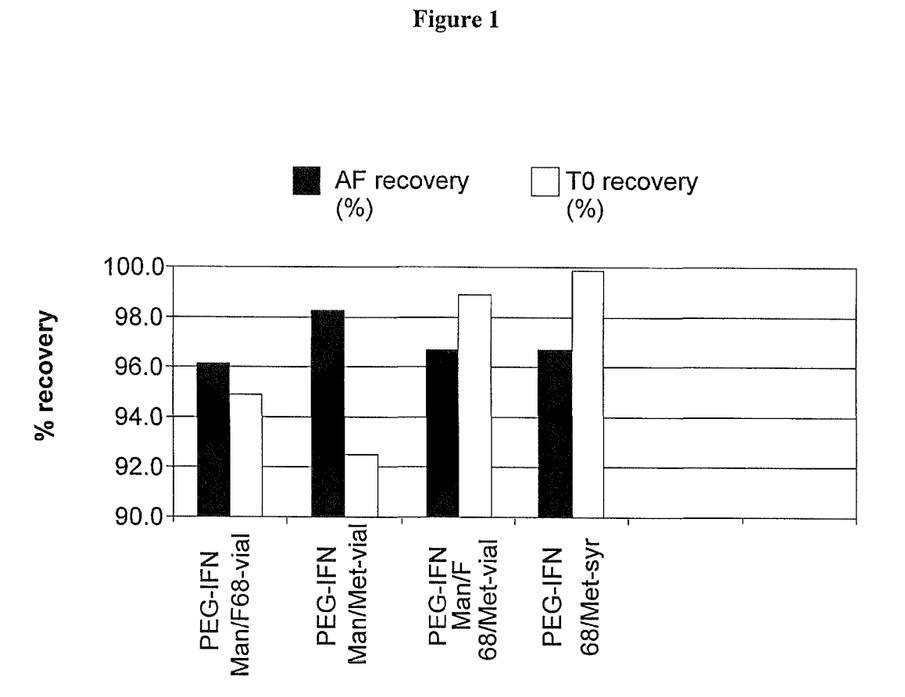
Figure 2:
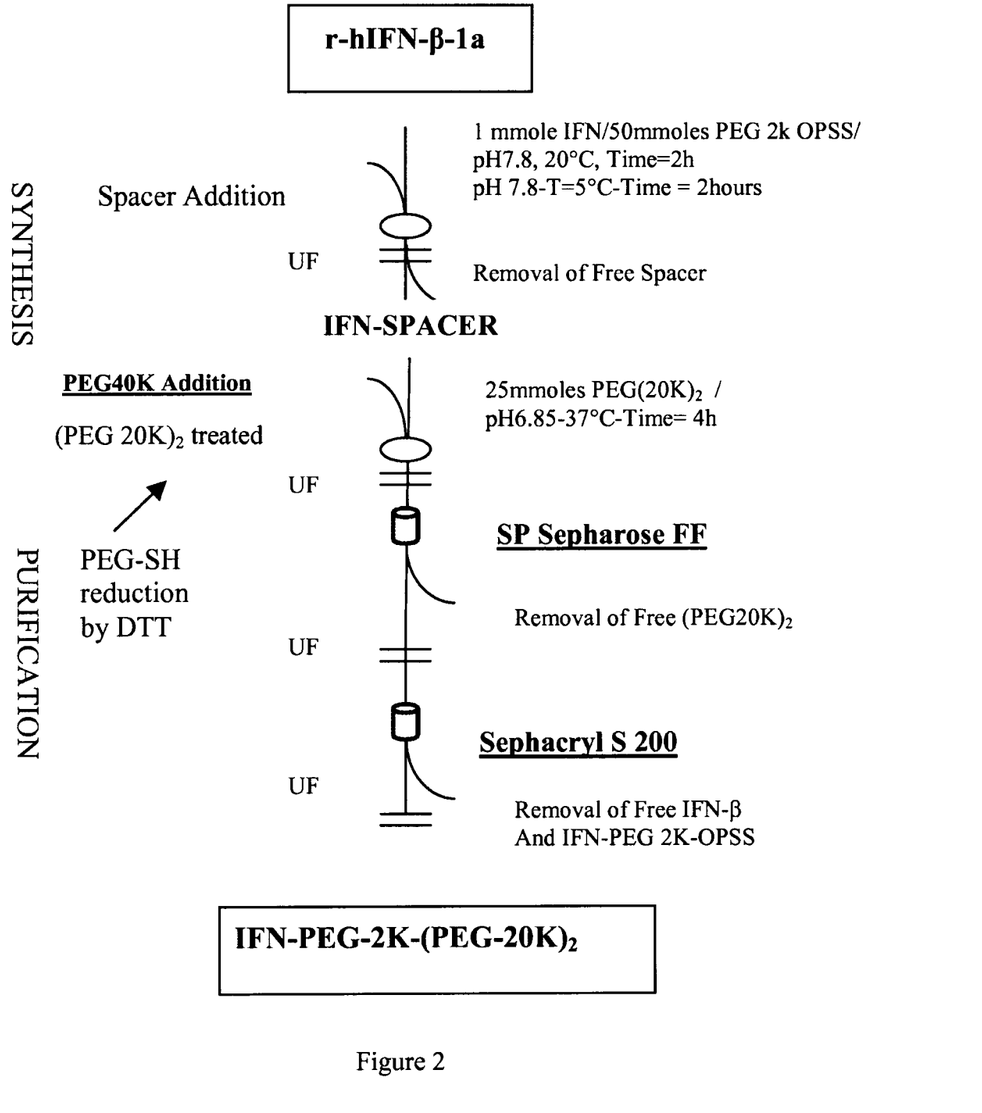
FIGS. 2 and 3 show PEG-IFN Flow charts of Synthesis and Purification. PEG 2k OPSS=(2-Pyridyldithiol)$_2$-PEG-2K; PEG (20K)$_2$=HS-Cysteamine-Lys-(PEG-20K)$_2$.
Figure 3:
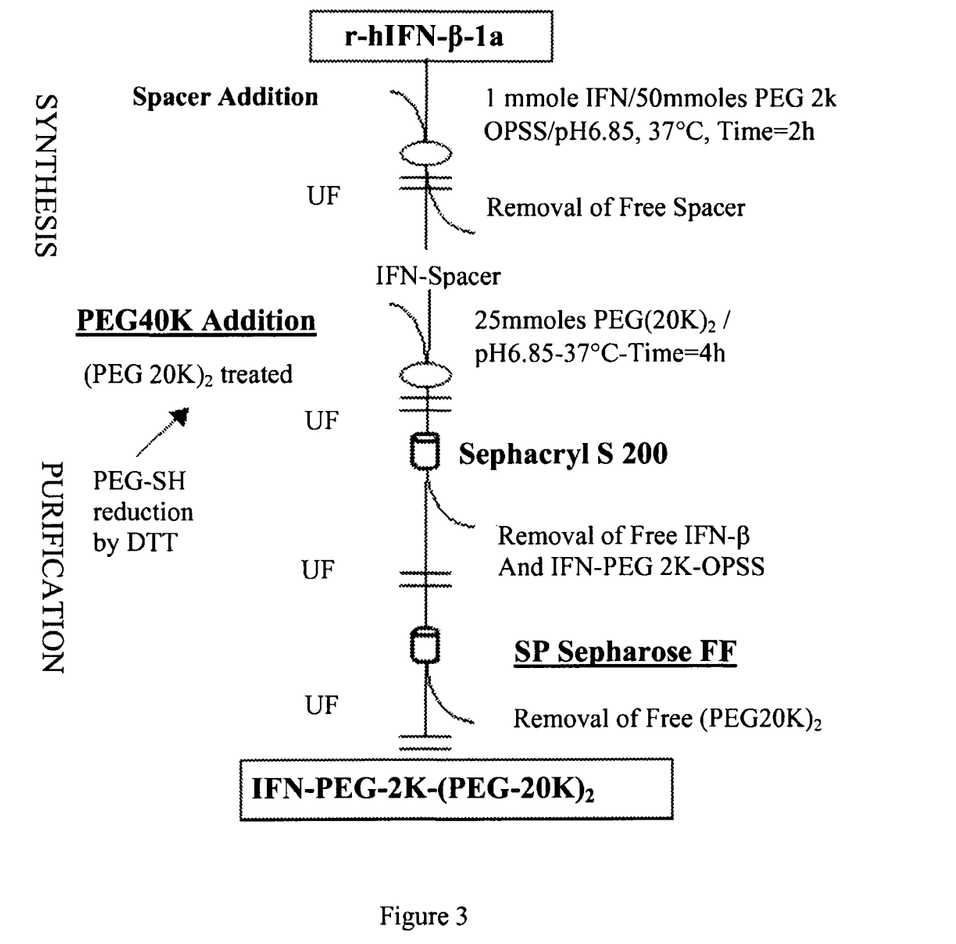

Preferred embodiments of the invention will be described by the following examples.
1. Preparation of a PEG-IFN-β conjugate
Examples of the preparation of PEG-IFN-β are depicted in FIGS. 2 and 3.
2. Formulation
PEG-IFN-β compositions were formulated using PEG-IFN-beta 1a. The solution was filtered though a 0.22 um membrane (Durapore) and filled into the final container (1 ml in vial or syringe).

The test composition contained 0.044 mg/ml PEG-IFN-beta 1a, 10 mM sodium acetate buffer pH 4.2, 45 mg/ml mannitol and 0.5 mg/ml Poloxamer 188. Alternatively, it contained 0.055 or 0.110 mg/ml PEG-IFN-beta 1a and possibly together with methionine.

Samples of the test composition were stored at 40° C., 25° C. and 2-8° C., respectively, and tests were performed for determination of purity by SE-HPLC or RP-HPLC, of protein content by SE-HPLC, of biological activity by an antiviral assay based on IFN-beta induced protection of cells and pH over time as well as measuring oxidized forms by peptide mapping/HPLC analysis.
3. Stability Assays and Other Experimentation
3.1. Purity and Assay by SE-HPLC
The purity by SE-HPLC was assessed on a Shodex column (Aqueous SE, code KW-803); the elution was performed in isocratic mode at 1.0 mL/min using PBS 1× prepared by a 10-fold dilution in water from PBS10× (Gibco BRL code 70013-016); the detection was performed by UV at 214 nm.

IFN-PEG formulated samples were injected using the following injection volumes: 200 mcL (for 44 and 55 mcg/mL samples; 100 mcL, for 110 mcg/mL samples).

For the assay, the protein quantification was performed against the reference standard PS200-01 (single point assay).

3.2. Purity by RP-HPLC

The purity by RP-HPLC was performed on a C4 column (Symmetry 300 C4, 5 m size 4.6×250 mm, Waters) thermostated at 35° C.; the wavelength was set at 214 nm and the elution performed at 1 mL/min using the following conditions:

Mobile phase: A=0.1% TFA/water; B=0.1% TFA/acetonitrile
Gradient: 30%→70% B in 40 min

| Time (min) | Flow (mL/min) | % A | % B |
|---|---|---|---|
| 0 | 1.0 | 70 | 30 |
| 3 | 1.0 | 70 | 30 |
| 40 | 1.0 | 30 | 70 |
| 45 | 1.0 | 70 | 30 |

IFN-PEG formulated samples were injected as it is using the following injection volumes: 160 mcL (for 44 mcg/mL samples); 200 mcL (for 55 mcg/mL samples); 100 mcL (for 110 mcg/mL samples).

3.3. Biological Activity (in Vitro Bioassay)

The biological activity was measured using the method available for IFN-β, which is an antiviral assay, based on the IFN-β induced protection of cells (WISH cells-human amniotic tissue) against the cytopathic effect of a virus (Vesicular Stomatitis Virus).

3.4. pH Determination

The pH measurements were performed using a calibrated pH meter (Mettler-Toledo, mod. 713) according to a standard operating procedure.

3.5. Oxidized Forms by Peptide Mapping/HPLC

The method for the quantification of the oxidized methionine residues (Met 1, Met 117, Met 36) foresees the proteolytic digestion of the IFN-PEG sample with Endoproteinase Lys-C, followed by a gradient HPLC analysis; a pre-treatment of the formulated sample is performed prior to the proteolytic digestion in order to remove any interference with the matrix components.

The separation of the proteolytic mixture is performed on an Acquity HPLC analytical column (BEH C18 1.7 μm 2.1× 50 mm cod.186000235D, Waters); the elution is performed in gradient conditions using 0.1% TFA/water (A1) and 0.1% TFA/acetonitrile (B1).

The following instrument settings and analysis parameters can be used:

| | |
|---|---|
| UV Detector wavelength | 214 nm |
| Autosampler Temperature | +5° C. ± 3° C. |
| Column Temperature | +40° C. ± 5° C. |
| Column flow rate | 0.6 mL/min |
| Analysis duration | 23 min |
| Next injection delay | 10 min |

| | Time (min) | Flow (mL/min) | A1 (%) | B1 (%) | Curve |
|---|---|---|---|---|---|
| Linear gradient: | 0 | 0.6 | 95 | 5 | — |
| | 1.0 | 0.6 | 95 | 5 | 6 |
| | 3.0 | 0.6 | 90 | 10 | 6 |
| | 8.0 | 0.6 | 64 | 36 | 6 |
| | 18.0 | 0.6 | 60 | 40 | 6 |
| | 20.0 | 0.6 | 0 | 100 | 6 |
| | 22.0 | 0.6 | 0 | 100 | 6 |
| | 23.0 | 0.6 | 95 | 5 | 6 |
| Total time analysis | 33 minutes | | | | |

TABLE 1

PEG-IFN-beta formulations composition (mg/mL)

| | PEG-IFN | Buffer | Mannitol | L-Methionine | Poloxamer 188 | Container |
|---|---|---|---|---|---|---|
| PEG-IFN Man/F68-vial | 0.044 | 10 mM acetate pH 4.2 (*) | 45.0 | — | 0.5 | DIN2R vial |
| PEG-IFN Man/Met-vial | 0.044 | 10 mM acetate pH 4.2 (*) | 45.0 | 0.12 | — | DIN2R vial |
| PEG-IFN Man/F68/Met-vial | 0.044 | 10 mM acetate pH 4.2 (*) | 45.0 | 0.12 | 0.5 | DIN2R vial |
| PEG-IFN Man/F68/Met-syr | 0.044 | 10 mM acetate pH 4.2 (*) | 45.0 | 0.12 | 0.5 | 1 mL syringe |

(*) Residual PBS buffer is also present from the bulk (due to 5-fold dilution of PEG-IFN drug substance)

TABLE 2

% Purity by SE-HPLC

| | Zero time Monomer | 1 Wk +40° C. Monomer | 2 Wks +40° C. Monomer | 4 Wks +40° C. Monomer |
|---|---|---|---|---|
| PEG-IFN Man/F68-vial | 85.2 | 83.3 | 82.1 | 79.8 |
| PEG-IFN Man/Met-vial | 85.3 | 84.3 | 82.2 | 80.3 |

TABLE 2-continued

| | % Purity by SE-HPLC | | | |
|---|---|---|---|---|
| PEG-IFN Man/F68/Met-vial | 85.0 | 83.0 | 81.1 | 78.7 |
| PEG-IFN Man/F68/Met-syr | 85.2 | 83.4 | 82.0 | 78.8 |

| | Zero time Monomer | 2 Wks +25° C. Monomer | 4 Wks +25° C. Monomer | 6 Wks +25° C. Monomer | 8 Wks +25° C. Monomer | 13 Wks +25° C. Monomer | 26 Wks +25° C. Monomer |
|---|---|---|---|---|---|---|---|
| PEG-IFN Man/F68-vial | 85.2 | 87.1 | 87.1 | 87.2 | 87.3 | 86.3 | 86.7 |
| PEG-IFN Man/Met-vial | 85.3 | 87.2 | 87.3 | 86.9 | 86.5 | 85.5 | 84.7 |
| PEG-IFN Man/F68/Met-vial | 85.0 | 87.0 | 86.7 | 86.8 | 86.7 | 85.8 | 86.1 |
| PEG-IFN Man/F68/Met-syr | 85.2 | 87.3 | 86.7 | 86.9 | 86.8 | 86.3 | 86.7 |

| | Zero time Monomer | 4 Wks +2-8° C. Monomer | 6 Wks +2-8° C. Monomer | 8 Wks +2-8° C. Monomer | 13 Wks +2-8° C. Monomer | 26 Wks +2-8° C. Monomer |
|---|---|---|---|---|---|---|
| PEG-IFN Man/F68-vial | 85.2 | 86.4 | 86.3 | 86.7 | 86.4 | 88.1 |
| PEG-IFN Man/Met-vial | 85.3 | 86.4 | 86.3 | 86.0 | 84.8 | 87.3 |
| PEG-IFN Man/F68/Met-vial | 85.0 | 85.8 | 85.9 | 85.7 | 85.7 | 87.5 |
| PEG-IFN Man/F68/Met-syr | 85.2 | 85.9 | 86.3 | 86.7 | 86.4 | 87.0 |

TABLE 3

| | % Purity by RP-HPLC | | | |
|---|---|---|---|---|
| | Zero Time | 1 W +40° C. | 2 Wks +40° C. | 4 Wks +40° C. |
| PEG-IFN Man/F68-vial | 96.0 | 94.1 | 91.7 | 87.4 |
| PEG-IFN Man/Met-vial | 96.3 | 93.9 | 90.8 | 88.5 |
| PEG-IFN Man/F68/Met-vial | 95.9 | 93.7 | 92.3 | 90.0 |
| PEG-IFN Man/F68/Met-syr | 96.4 | 93.4 | 92.5 | 88.8 |

| | Zero Time | 2 Wks +25° C. | 4 Wks +25° C. | 6 Wks +25° C. | 8 Wks +25° C. | 12 Wks +25° C. | 26 Wks +25° C. |
|---|---|---|---|---|---|---|---|
| PEG-IFN Man/F68-vial | 96.0 | 95.0 | 94.5 | 93.3 | 93.5 | 93.9 | 90.6 |
| PEG-IFN Man/Met-vial | 96.3 | 94.3 | 95.0 | 93.4 | 93.3 | 94.1 | 90.9 |
| PEG-IFN Man/F68/Met-vial | 95.9 | 94.5 | 94.4 | 93.4 | 93.1 | 94.3 | 90.8 |
| PEG-IFN Man/F68/Met-syr | 96.4 | 94.3 | 94.3 | 93.3 | 93.4 | 93.1 | 90.6 |

| | Zero Time | 4 Wks +2-8° C. | 6 Wks +2-8° C. | 8 Wks +2-8° C. | 12 Wks +2-8° C. | 26 Wks +2-8° C. |
|---|---|---|---|---|---|---|
| PEG-IFN Man/F68-vial | 96.0 | 94.5 | 94.9 | 94.4 | 95.7 | 96.0 |
| PEG-IFN Man/Met-vial | 96.3 | 95.2 | 93.9 | 94.0 | 95.1 | 95.8 |
| PEG-IFN Man/F68/Met-vial | 95.9 | 94.9 | 94.5 | 93.9 | 95.3 | 95.7 |
| PEG-IFN Man/F68/Met-syr | 96.4 | 94.7 | 94.1 | 94.6 | 94.7 | 96.1 |

TABLE 4

| | Titre (mcg/mL) by SE-HPLC | | | |
|---|---|---|---|---|
| | Zero Time | 1 Wk +40° C. | 2 Wks +40° C. | 4 Wks +40° C. |
| PEG-IFN Man/F68-vial | 41.2 | 44.4 | 44.3 | 43.7 |
| PEG-IFN Man/Met-vial | 40.5 | 43.1 | 43.3 | 41.5 |
| PEG-IFN Man/F68/Met-vial | 43.0 | 46.3 | 45.3 | 44.9 |
| PEG-IFN Man/F68/Met-syr | 43.4 | 46.7 | 46.0 | 45.7 |
| | Zero Time | 2 Wks +25° C. | 4 Wks +25° C. | 6 Wks +25° C. | 8 Wks +25° C. | 12 Wks +25° C. | 26 Wks +25° C. |
| PEG-IFN Man/F68-vial | 41.2 | 43.6 | 42.7 | 41.9 | 44.5 | 41.8 | 41.4 |
| PEG-IFN Man/Met-vial | 40.5 | 42.0 | 41.2 | 40.4 | 42.7 | 40.6 | 38.4 |
| PEG-IFN Man/F68/Met-vial | 43.0 | 45.1 | 44.2 | 43.3 | 45.7 | 43.1 | 42.5 |
| PEG-IFN Man/F68/Met-syr | 43.4 | 45.6 | 44.6 | 43.7 | 46.2 | 43.8 | 43.4 |
| | Zero Time | 4 Wks +2-8° C. | 6 Wks +2-8° C. | 8 Wks +2-8° C. | 12 Wks +2-8° C. | 26 Wks +2-8° C. |
| PEG-IFN Man/F68-vial | 41.2 | 42.7 | 42.0 | 44.4 | 42.2 | 41.9 |
| PEG-IFN Man/Met-vial | 40.5 | 41.7 | 40.4 | 43.3 | 41.1 | 39.9 |
| PEG-IFN Man/F68/Met-vial | 43.0 | 44.4 | 43.3 | 45.7 | 43.6 | 43.3 |
| PEG-IFN Man/F68/Met-syr | 43.4 | 44.7 | 44.1 | 46.4 | 44.3 | 44.2 |

TABLE 5

| | Titre (mcg/mL) by SE-HPLC | | | | |
|---|---|---|---|---|---|
| | Before Filtration (mcg/mL) | After Filtration (mcg/mL) | T0 (mcg/mL) | AF recovery (%) | T0 recovery (%) |
| PEG-IFN Man/F68-vial | 43.4 | 41.7 | 41.2 | 96.1 | 94.9 |
| PEG-IFN Man/Met-vial | 43.4 | 42.7 | 40.2 | 98.3 | 92.5 |
| PEG-IFN Man/F68/Met-vial | 43.5 | 42.0 | 43.0 | 96.7 | 98.9 |
| PEG-IFN Man/F68/Met-syr | 43.5 | 42.0 | 43.4 | 96.7 | 99.9 |

TABLE 6

| | pH determination | | | | |
|---|---|---|---|---|---|
| | Zero Time | 4 Wks +25° C. | 8 Wks +25° C. | 12 Wks +25° C. | 26 Wks +25° C. |
| PEG-IFN Man/F68-vial | 4.22 | 4.20 | 4.16 | 4.19 | 4.22 |
| PEG-IFN Man/Met-vial | 4.23 | 4.20 | 4.17 | 4.21 | 4.20 |
| PEG-IFN Man/F68/Met-vial | 4.22 | 4.21 | 4.19 | 4.23 | 4.22 |
| PEG-IFN Man/F68/Met-syr | 4.22 | 4.20 | 4.19 | 4.22 | 4.21 |

TABLE 6-continued

| pH determination | | | | | |
|---|---|---|---|---|---|
| | Zero Time | 4 Wks +2-8° C. | 8 Wks +2-8° C. | 12 Wks +2-8° C. | 26 Wks +2-8° C. |
| PEG-IFN Man/F68-vial | 4.22 | 4.22 | 4.17 | 4.21 | 4.17 |
| PEG-IFN Man/Met-vial | 4.23 | 4.23 | 4.17 | 4.19 | 4.18 |
| PEG-IFN Man/F68/Met-vial | 4.22 | 4.25 | 4.19 | 4.23 | 4.20 |
| PEG-IFN Man/F68/Met-syr | 4.22 | 4.26 | 4.18 | 4.24 | 4.22 |

TABLE 7

Bioassay (MIU/mL) MIU/mL

| | Zero Time | 4 Wks +25° C. | 8 Wks +25° C. | 12 Wks +25° C. | 26 Wks +25° C. |
|---|---|---|---|---|---|
| PEG-IFN Man/F68/Met-vial | 33.9 | 36.6 | 35.7 | 33.6 | 27.0 |
| PEG-IFN Man/F68/Met-syr | 34.8 | 37.9 | 40.1 | 32.6 | 30.2 |

| | Zero Time | 4 Wks +2-8° C. | 8 Wks +2-8° C. | 12 Wks +2-8° C. | 26 Wks +2-8° C. |
|---|---|---|---|---|---|
| PEG-IFN Man/F68/Met-vial | 33.9 | 38.8 | 36.8 | 34.0 | 31.5 |
| PEG-IFN Man/F68/Met-syr | 34.8 | 38.1 | 40.1 | 34.5 | 31.3 |

TABLE 8

Purity by SE-HPLC (%)

40° C.

| | T = 0 | | 1 Wk | | 2 Wks | | 4 Wks | |
|---|---|---|---|---|---|---|---|---|
| | HMW + Dim | Monomer | HMW + Dim | Monomer | HMW + Dim | Monomer | HMW + Dim | Monomer |
| PEG-IFN/Acet 55 mcg | 3.5 | 96.5 | 4.0 | 96.0 | 3.8 | 96.2 | 4.4 | 95.6 |
| PEG-IFN/Acet 55 mcg/0.25 Met | 3.5 | 96.5 | 3.8 | 96.2 | 4.1 | 95.9 | 4.4 | 95.7 |
| PEG-IFN/Acet 110 mcg | 3.6 | 96.4 | 4.5 | 95.5 | 5.6 | 94.4 | 5.7 | 94.3 |
| PEG-IFN/Acet 110 mcg/0.25 Met | 3.9 | 96.1 | 4.3 | 95.7 | 4.5 | 95.5 | 5.1 | 94.9 |

25° C.

| | T = 0 | | 4 Wks | | 8 Wks | | 13 Wks | |
|---|---|---|---|---|---|---|---|---|
| | HMW + Dim | Monomer | HMW + Dim | Monomer | HMW + Dim | Monomer | HMW + Dim | Monomer |
| PEG-IFN/Acet 55 mcg | 3.5 | 96.5 | 3.4 | 96.6 | 3.6 | 96.4 | 3.5 | 96.5 |
| PEG-IFN/Acet 55 mcg/0.25 Met | 3.5 | 96.5 | 3.3 | 96.7 | 3.6 | 96.4 | 3.5 | 96.5 |
| PEG-IFN/Acet 110 mcg | 3.6 | 96.4 | 3.7 | 96.3 | 4.0 | 96.0 | 3.7 | 96.3 |
| PEG-IFN/Acet 110 mcg/0.25 Met | 3.9 | 96.1 | 3.7 | 96.3 | 4.0 | 96.1 | 3.9 | 96.1 |

2-8° C.

| | T = 0 | | 4 Wks | | 8 Wks | | 13 Wks | |
|---|---|---|---|---|---|---|---|---|
| | HMW + Dim | Monomer | HMW + Dim | Monomer | HMW + Dim | Monomer | HMW + Dim | Monomer |
| PEG-IFN/Acet 55 mcg | 3.5 | 96.5 | 3.9 | 96.1 | 3.8 | 96.2 | 3.6 | 96.4 |
| PEG-IFN/Acet 55 mcg/0.25 Met | 3.5 | 96.5 | 3.6 | 96.4 | 4.0 | 96.0 | 3.6 | 96.4 |

TABLE 8-continued

| Purity by SE-HPLC (%) | | | | | | | | |
|---|---|---|---|---|---|---|---|---|
| PEG-IFN/Acet 110 mcg | 3.6 | 96.4 | 3.9 | 96.1 | 4.2 | 95.8 | 3.9 | 96.1 |
| PEG-IFN/Acet 110 mcg/0.25 Met | 3.9 | 96.1 | 3.9 | 96.1 | 4.1 | 95.9 | 3.8 | 96.2 |

TABLE 9

Protein content by SE-HPLC (mcg/mL)

40° C.

| | T = 0 | 1 Wk | 2 Wks | 4 Wks |
|---|---|---|---|---|
| PEG-IFN/Acet 55 mcg | 52.7 | 51.9 | 52.3 | 51.9 |
| PEG-IFN/Acet 55 mcg/0.25 Met | 53.0 | 52.1 | 52.2 | 51.8 |
| PEG-IFN/Acet 110 mcg | 110.2 | 109.1 | 107.9 | 108.0 |
| PEG-IFN/Acet 110 mcg/0.25 Met | 110.9 | 108.7 | 107.9 | 107.5 |

| | T = 0 | 4 Wks | 8 Wks | 13 Wks |
|---|---|---|---|---|
| 25° C. | | | | |
| PEG-IFN/Acet 55 mcg | 52.7 | 52.5 | 53.0 | 51.6 |
| PEG-IFN/Acet 55 mcg/0.25 Met | 53.0 | 53.4 | 53.1 | 51.2 |
| PEG-IFN/Acet 110 mcg | 110.2 | 110.0 | 109.5 | 107.0 |
| PEG-IFN/Acet 110 mcg/0.25 Met | 110.9 | 109.6 | 109.1 | 106.7 |
| 2-8° C. | | | | |
| PEG-IFN/Acet 55 mcg | 52.7 | 54.4 | 53.8 | 51.9 |
| PEG-IFN/Acet 55 mcg/0.25 Met | 53.0 | 54.0 | 53.7 | 52.4 |
| PEG-IFN/Acet 110 mcg | 110.2 | 111.1 | 110.5 | 108.6 |
| PEG-IFN/Acet 110 mcg/0.25 Met | 110.9 | 111.0 | 110.5 | 108.3 |

TABLE 10

Purity by RP-HPLC (%)

40° C.

| | T = 0 | 1 Wk | 2 Wks | 4 Wks |
|---|---|---|---|---|
| PEG-IFN/Acet 55 mcg | 97.6 | 96.1 | 94.4 | 94.6 |
| PEG-IFN/Acet 55 mcg/0.25 Met | 97.7 | 95.7 | 94.2 | 94.6 |
| PEG-IFN/Acet 110 mcg | 95.9 | 95.5 | 93.8 | 94.4 |
| PEG-IFN/Acet 110 mcg/0.25 Met | 96.0 | 95.7 | 93.7 | 94.2 |

| | T = 0 | 4 Wks | 8 Wks | 13 Wks |
|---|---|---|---|---|
| 25° C. | | | | |
| PEG-IFN/Acet 55 mcg | 98.7 | 98.3 | 96.5 | 97.3 |
| PEG-IFN/Acet 55 mcg/0.25 Met | 98.7 | 98.8 | 96.8 | 96.2 |
| PEG-IFN/Acet 110 mcg | 97.0 | 98.6 | 96.8 | 96.5 |
| PEG-IFN/Acet 110 mcg/0.25 Met | 97.0 | 98.5 | 96.5 | 95.9 |

TABLE 10-continued

Purity by RP-HPLC (%)

2-8° C.

| | | | | |
|---|---|---|---|---|
| PEG-IFN/Acet 55 mcg | 98.7 | 99.3 | 98.1 | 98.6 |
| PEG-IFN/Acet 55 mcg/0.25 Met | 98.7 | 99.6 | 98.3 | 98.4 |
| PEG-IFN/Acet 110 mcg | 97.0 | 98.3 | 96.8 | 96.6 |
| PEG-IFN/Acet 110 mcg/0.25 Met | 97.0 | 98.3 | 96.7 | 96.9 |

TABLE 11 pH values

| | T = 0 | 4 Wks | 8 Wks | 13 Wks |
|---|---|---|---|---|
| 25° C. | | | | |
| PEG-IFN/Acet 55 mcg | 4.22 | 4.21 | 4.22 | 4.12 |
| PEG-IFN/Acet 55 mcg/0.25 Met | 4.21 | 4.19 | 4.23 | 4.21 |
| PEG-IFN/Acet 110 mcg | 4.21 | 4.15 | 4.25 | 4.21 |
| PEG-IFN/Acet 110 mcg/0.25 Met | 4.20 | 4.15 | 4.19 | 4.19 |
| 2-8° C. | | | | |
| PEG-IFN/Acet 55 mcg | 4.22 | 4.15 | 4.17 | 4.19 |
| PEG-IFN/Acet 55 mcg/0.25 Met | 4.21 | 4.16 | 4.19 | 4.21 |
| PEG-IFN/Acet 110 mcg | 4.21 | 4.15 | 4.17 | 4.20 |
| PEG-IFN/Acet 110 mcg/0.25 Met | 4.20 | 4.16 | 4.15 | 4.19 |

TABLE 12

Bioassay (U/mL)

| | T = 0 | 4 Wks | 8 Wks | 13 Wks |
|---|---|---|---|---|
| 25° C. | | | | |
| PEG-IFN/Acet 55 mcg | 40.3 | 36.0 | 32.7 | 32.4 |
| PEG-IFN/Acet 55 mcg/0.25 Met | 38.7 | 33.0 | 34.9 | 30.0 |
| PEG-IFN/Acet 110 mcg | 81.9 | 65.7 | 70.8 | 63.9 |
| PEG-IFN/Acet 110 mcg/0.25 Met | 77.0 | 63.7 | 72.9 | 65.6 |
| 2-8° C. | | | | |
| PEG-IFN/Acet 55 mcg | 40.3 | 40.7 | 34.9 | 28.0 |
| PEG-IFN/Acet 55 mcg/0.25 Met | 38.7 | 40.1 | 35.7 | 27.4 |
| PEG-IFN/Acet 110 mcg | 81.9 | 68.8 | 72.0 | 57.7 |
| PEG-IFN/Acet 110 mcg/0.25 Met | 77.0 | 75.3 | 70.0 | 56.8 |

TABLE 13

Oxidized forms by peptide mapping/UPLC (%)

2-8° C.

| | T = 0 | 8 Wks | 13 Wks | Slope (%/Mo) |
|---|---|---|---|---|
| Met 1 | | | | |
| PEG-IFN/Acet 55 mcg/No Met | 1.7 | 2.0 | 1.3 | −0.09 |
| PEG-IFN/Acet 55 mcg/0.25 Met | 1.6 | 1.5 | 1.2 | −0.13 |
| PEG-IFN/Acet 110 mcg/No Met | 1.5 | 1.6 | 1.3 | −0.03 |
| PEG-IFN/Acet 110 mcg/0.25 Met | 1.3 | 1.6 | 1.3 | 0.02 |

TABLE 13-continued

| Oxidized forms by peptide mapping/UPLC (%) | | | | |
|---|---|---|---|---|
| Met 117 | | | | |
| PEG-IFN/Acet 55 mcg/No Met | 4.6 | 5.5 | 5.3 | 0.24 |
| PEG-IFN/Acet 55 mcg/0.25 Met | 4.8 | 4.7 | 4.4 | −0.10 |
| PEG-IFN/Acet 110 mcg/No Met | 5.0 | 5.1 | 5.1 | 0.06 |
| PEG-IFN/Acet 110 mcg/0.25 Met | 5.3 | 5.1 | 4.5 | −0.24 |
| Met 36 | | | | |
| PEG-IFN/Acet 55 mcg/No Met | 4.0 | 4.3 | 4.7 | 0.21 |
| PEG-IFN/Acet 55 mcg/0.25 Met | 4.2 | 3.8 | 4.0 | −0.07 |
| PEG-IFN/Acet 110 mcg/No Met | 3.8 | 4.2 | 4.5 | 0.24 |
| PEG-IFN/Acet 110 mcg/0.25 Met | 3.9 | 3.9 | 4.0 | 0.03 |
| | 0 | 2 | 3 | |

| 25° C. | | | | |
|---|---|---|---|---|
| | T = 0 | 4 Wks | 8 Wks | 13 Wks | Slope (%/Mo) |
| Met 1 | | | | |
| PEG-IFN/Acet 55 mcg/No Met | 1.7 | 1.4 | 1.9 | 1.6 | 0.01 |
| PEG-IFN/Acet 55 mcg/0.25 Met | 1.6 | 1.2 | 1.8 | 1.3 | −0.03 |
| PEG-IFN/Acet 110 mcg/No Met | 1.5 | — | 1.9 | 1.5 | 0.05 |
| PEG-IFN/Acet 110 mcg/0.25 Met | 1.3 | 1.2 | 1.7 | 1.3 | 0.06 |
| Met 117 | | | | |
| PEG-IFN/Acet 55 mcg/No Met | 4.6 | 4.2 | 5.4 | 5.2 | 0.29 |
| PEG-IFN/Acet 55 mcg/0.25 Met | 4.8 | 4.4 | 4.9 | 4.7 | 0.02 |
| PEG-IFN/Acet 110 mcg/No Met | 5.0 | — | 5.2 | 5.0 | 0.02 |
| PEG-IFN/Acet 110 mcg/0.25 Met | 5.3 | 4.4 | 5.0 | 4.5 | −0.20 |
| Met 36 | | | | |
| PEG-IFN/Acet 55 mcg/No Met | 4.0 | 3.5 | 4.6 | 4.8 | 0.36 |
| PEG-IFN/Acet 55 mcg/0.25 Met | 4.2 | 3.4 | 3.7 | 4.1 | 0.02 |
| PEG-IFN/Acet 110 mcg/No Met | 3.8 | — | 4.3 | 4.6 | 0.26 |
| PEG-IFN/Acet 110 mcg/0.25 Met | 3.9 | 3.6 | 3.8 | 4.0 | 0.06 |
| | 0 | 1 | 2 | 3 | |

NB: In all Tables, mcg stands for microgrammes, HMW for high molecular weight species, Dim for dimer, Mo for month.

Reference List

1. Derynk R. et al., Nature 1980; 285, 542-547;
2. Familletti, P. C., Rubinstein, S., and Pestka, S. 1981 "A Convenient and Rapid Cytopathic Effect Inhibition Assay for Interferon," in Methods in Enzymology, Vol. 78 (S. Pestka, ed.), Academic Press, New York, 387-394;
3. Mark D. F. et al., Proc. Natl. Acad. Sci. U.S.A., 81 (18) 5662-5666 (1984);
4. Pestka, S. (1986) "Interferon Standards and General Abbreviations, in Methods in Enzymology (S. Pestka, ed.), Academic Press, New York 119, 14-23;
5. Rubinstein, S., Familletti, P. C., and Pestka, S. Convenient Assay for Interferons. J. Virol 1981; 37, 755-758;
6. Shepard H. M. et al., Nature 1981; 294, 563-565.
7. Woghiren et al. in Bioconjugate Chem., 4(5): 314-318, 1993.

The invention claimed is:

1. A liquid pharmaceutical composition comprising an interferon-β pegylated with polyethylene glycol (PEG) having a molecular weight of at least 20kDa (PEG-IFN-β), a polyol excipient at a concentration of about 30 mg/ml to about 50 mg/ml, a poloxamer surfactant and a sodium acetate buffer, wherein the pH of the pharmaceutical composition is 4.2 ±0.2, and wherein the poloxamer surfactant is poloxamer 188.

2. The composition according to claim 1, wherein said PEG-IFN-β is present at a concentration of about 0.01 mg/ml to about 0.1 mg/ml.

3. The composition according to claim 1, wherein said PEG-IFN-β is present at a concentration of about 0.044 mg/ml, 0.055 mg/ml or 0.110 mg/ml.

4. The composition according to claim 1, wherein the PEG is linear or branched polyethylene glycol (PEG).

5. The composition according to claim 1, wherein the PEG has a molecular weight of 40 kDa.

6. The composition according to claim 1, wherein the PEG is linked to the INF-β by a spacer.

7. The composition according to claim 6, wherein the spacer has a molecular weight of 100 to 5000 daltons.

8. The composition according to claim 7, wherein the spacer has a molecular weight of 1500 to 2500 daltons.

9. The composition according to claim 7, wherein the spacer has a molecular weight of 2000 daltons.

10. The composition according to claim 1, wherein said excipient is present at a concentration of about 40 mg/ml to about 50 mg/ml.

11. The composition according to claim 1, wherein said excipient is present at a concentration of about 45 mg/ml.

12. The composition according to claim 1, wherein said poloxamer surfactant is present at a concentration of about 0.1 mg/ml to about 1 mg/ml.

13. The composition according to claim 1, wherein said poloxamer surfactant is present at a concentration of about 0.4 mg/ml to about 0.7 mg/ml.

14. The composition according to claim 1, wherein said poloxamer surfactant is present at a concentration of about 0.5 mg/ml.

15. The composition according to claim 1, wherein said buffer is present at a concentration of about 5 mM to 500 mM.

16. The composition according to claim 15, wherein said buffer is present at a concentration of about 10 mM.

17. The composition according to claim 1, wherein said composition is an aqueous solution.

18. The composition according to claim 1, wherein said composition further comprises methionine.

19. The composition according to claim 18, wherein methionine is present in a concentration of 0.10 to 0.50 mg/ml.

20. The composition according to claim 18, wherein methionine is present in a concentration of 0.12 to 0.25 mg/ml.

21. The composition according to claim 18, wherein methionine is present in a concentration of 0.1 to 0.3 mg/ml.

22. The composition according to claim 18, wherein methionine is present in a concentration of 0.12 mg/ml.

23. The composition according to claim 18, wherein methionine is present in a concentration of 0.25 mg/ml.

24. The composition according to claim 1, wherein said composition comprises 0.044 mg/ml PEG-IFN-β, 10 mM sodium acetate buffer at about pH of 4.2, 45 mg/ml mannitol and 0.5 mg/ml Poloxamer 188.

25. The composition according to claim 1, wherein said composition comprises 0.044 mg/ml PEG-IFN-β, 10 mM sodium acetate buffer at a pH of 4.2, 45 mg/ml mannitol and 0.5 mg/ml Poloxamer 188.

26. The composition according to claim 1, wherein said composition comprises 0.044 mg/ml PEG-IFN-β, 10 mM sodium acetate buffer at about pH of 4.2 ±0.2, 45 mg/ml mannitol and 0.5 mg/ml Poloxamer 188.

27. A container hermetically sealed in conditions sterile and appropriate for storage prior to use, comprising the liquid pharmaceutical formulation according to claim 1.

28. The container according to claim 1, wherein said container is a pre-filled syringe, or a vial for an auto-injector.

29. A method for preparing a liquid pharmaceutical composition according to claim 1, wherein said method comprises adding a calculated amount of excipient and poloxamer surfactant to a buffered solution and adding pegylated IFN-β.

* * * * *

UNITED STATES PATENT AND TRADEMARK OFFICE
CERTIFICATE OF CORRECTION

PATENT NO.           : 9,138,403 B2
APPLICATION NO.      : 12/738375
DATED                : September 22, 2015
INVENTOR(S)          : Alessandra Del Rio and Joel Richard It is certified that error appears in the above-identified patent and that said Letters Patent is hereby corrected as shown below:

In the Specification

Column 3,
Line 27, "HOCH$_2$CH$_2$-O-(CH$_2$CH$_2$O)nCH$_2$CH$_2$OH" should read
--HOCH$_2$CH$_2$O(CH$_2$CH$_2$O)nCH$_2$CH$_2$OH--.

Column 7,
Line 2, "the IFN-ft" should read --the IFN-β.--.
Line 25, "Y-CH$_2$CH$_2$-O-(CH$_2$CH$_2$O)$m$CH$_2$CH$_2$-Z" should read
--Y-CH$_2$CH$_2$O(CH$_2$CH$_2$O)mCH$_2$CH$_2$-Z--.

Column 8,
Lines 22-23, "interferon-β," should read --interferon-β),--.

Column 16,
Line 8, "Acquity HPLC" should read --Acquity UPLC--.
Line 9, "cod. 186000235D, Waters" should read --cod. 1860002350, Waters--.

In the Claims

Column 28,
Line 35, "according to claim 1" should read --according to claim 27--.

Signed and Sealed this
Nineteenth Day of April, 2016

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial sequence
<220> FEATURE:
<223> OTHER INFORMATION: amino acid linker sequence

<400> SEQUENCE: 1

Glu Phe Gly Ala Gly Leu Val Leu Gly Gly Gln Phe Met
1               5                   10
```